United States Patent [19]

Richter et al.

[11] 4,203,019
[45] May 13, 1980

[54] METHOD FOR PRODUCING A SEALED CONTAINER BY VACUUM WELDING

[75] Inventors: Gerolf Richter; Scott B. Shanks, both of Berlin, Fed. Rep. of Germany

[73] Assignee: Biotronik Mess- und Therapiegeräte GmbH & Co., Berlin, Fed. Rep. of Germany

[21] Appl. No.: 899,784

[22] Filed: Apr. 25, 1978

[30] Foreign Application Priority Data

Apr. 29, 1977 [DE] Fed. Rep. of Germany ....... 2719884

[51] Int. Cl.² ..................... B23K 31/02; B23K 15/00
[52] U.S. Cl. ............................ 219/72; 219/121 EM; 228/184; 220/DIG. 29
[58] Field of Search ........... 219/72, 121 EB, 121 EM; 128/419 P, 419 PS; 228/103, 104, 184; 220/256, DIG. 29; 53/80, 81, 82, 83

[56] References Cited

U.S. PATENT DOCUMENTS

| | | | |
|---|---|---|---|
| 2,263,021 | 11/1941 | Vecker | 220/DIG. 29 X |
| 3,719,791 | 3/1973 | Peyrot | 219/121 EB |
| 3,818,304 | 6/1974 | Hursen et al. | 128/419 PS X |
| 3,857,738 | 12/1974 | Brown | 128/419 PS X |
| 3,939,880 | 2/1976 | Zook et al. | 219/72 X |
| 4,117,300 | 9/1978 | Ricards | 220/DIG. 29 X |

FOREIGN PATENT DOCUMENTS

| | | | |
|---|---|---|---|
| 648528 | 8/1937 | Fed. Rep. of Germany . | |
| 2050621 | 4/1971 | France | 219/121 EM |
| 166852 | 4/1934 | Switzerland . | |
| 1146214 | 3/1969 | United Kingdom | 219/121 EB |

*Primary Examiner*—B. A. Reynolds
*Assistant Examiner*—Keith E. George
*Attorney, Agent, or Firm*—Spencer & Kaye

[57] ABSTRACT

Method for producing a container whose interior is substantially under atmospheric pressure, by a vacuum welding process in which the container is sealed by welding together under vacuum a plurality of wall components while maintaining an opening therein. The interior of the container is filled through the opening with a medium which is substantially under atmospheric pressure. The opening is made vacuum-tight by a first seal. The container interior is sealed from the outside by an additional seal in the form of a cover for the opening, which cover is welded to the container under vacuum. The cover borders on the outer face of the container in such a manner that the cover is welded to the container under vacuum along a line which extends at such a distance from the first seal that the sealing effect of the first seal is not adversely influenced.

20 Claims, 7 Drawing Figures

METHOD FOR PRODUCING A SEALED CONTAINER BY VACUUM WELDING

BACKGROUND OF THE INVENTION

The present invention relates to a method for producing a container whose interior is substantially under atmospheric pressure, by means of a vacuum welding process.

In a number of applications, it is necessary for a container which is hermetically sealed under vacuum to have substantially atmospheric pressure in its interior because devices or objects disposed therein must remain subjected to such a defined pressure of a given gas or gas mixture.

In particular, containers in the form of housings for implantable cardiac pacemakers must be tightly and hermetically sealed so that aggressive body fluids cannot reach the interior. If body fluids penetrated into the interior, they would cause irreversible damage in the components which may result in malfunction of the pacemaker. In order to attain a high sealing effect with high resistance to the attack of body fluids, a cobalt alloy is used for the housing which is sealed under vacuum by means of electron beam welding.

In order to be able to operate, certain types of primary elements used to supply the electronic circuit of the pacemaker with current require ambient pressure in the order of magnitude of atmospheric pressure. In some types of pacemakers, the gas with which the interior of the housing is filled under atmospheric pressure is helium.

In order to prevent the gas used to fill the interior from flowing out, it is necessary to seal the housing. This is accomplished in many cases by first welding the housing wall components together under vacuum while leaving an opening, removing the vacuum and then filling the interior of the housing through the opening with gas under atmospheric pressure, and thereafter soldering the opening under pressure conditions which correspond to those in the housing interior. Instead of soldering, the remaining opening can be closed by casting with plastic or by resistance welding in a similar manner.

This process has the drawback that the housing is not sealed completely hermetically by a uniform welding process. The advantages of a weld connection produced by means of an electron beam under vacuum cannot become effective, for example, unless all housing openings are welded shut according to this method, since the total properties of the container and its usefulness are significantly reduced by but a single weak point.

SUMMARY OF THE INVENTION

It is a primary object of the present invention to provide a method for vacuum welding of a container whose interior is substantially under atmospheric pressure in which a remaining opening for filling in a medium that is under atmospheric pressure can also be welded shut under vacuum so that the entire container is sealed according to a uniform method.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects, and in accordance with its purpose, the present invention, as embodied and broadly described, provides a method for producing a container whose interior is substantially under atmospheric pressure by means of a vacuum welding process, which comprises: sealing the container by welding together under vacuum a plurality of wall components while maintaining an opening in the container; filling the interior of the container through the opening with a medium which is substantially under atmospheric pressure; sealing the opening of the filled container to be vacuum-tight by means of a first sealing means; and sealing the container interior from the outside by an additional seal in the form of a cover for the opening by vacuum welding the cover to the container, with the cover bordering the outer face of the container in such a manner that the cover is welded under vacuum along a line which extends at such a distance from the first sealing means that the sealing effect of the first sealing means is not adversely influenced during the vacuum welding of the additional seal.

It is of particular advantage in the present invention, in addition to the fact that all weld seams facing the outside can be produced according to the same welding process, that when a material of a certain wall thickness is used, the container, once it has been sealed, will have at least this wall thickness everywhere. Moreover, the significant outer weld connections can be produced and controlled in an economical manner with the same fabrication tools.

It is to be understood that both the foregoing general description and the following detailed description are exemplary, but are not restrictive of the invention.

BRIEF DESCRIPTION OF THE DRAWINGS

The accompanying drawings, in which like numbers indicate like parts, illustrate examples of presently preferred embodiments of the invention and, together with the description, serve to explain the principles of the invention.

DETAILED DESCRIPTION OF THE INVENTION

Figure 1:
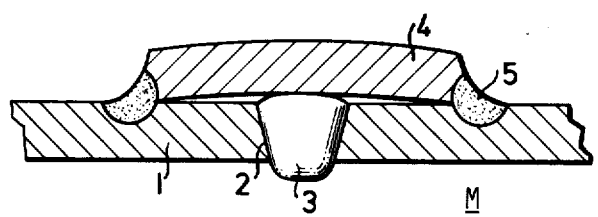
FIG. 1 is a cross-sectional view of the area of an opening of a container which is sealed according to a first embodiment of the method of the present invention.

In the practice of the present invention, there are two separate vacuum welding stages. In the initial vacuum welding stage, a plurality of container wall components are sealed to each other by vacuum welding to form a housing while maintaining an opening in the container.

Generally, only one opening is maintained which remains after the initial vacuum welding stage so that except for this one opening, all outer openings have now been closed by vacuum welding so that all weld seams which face the outside are produced by the same welding process. After this initial vacuum welding, the interior of the container is filled through the opening with gas under atmospheric pressure. The opening is then closed by a preliminary seal or first sealing means to seal the opening to be vacuum-tight and prevent escape of the gas under vacuum conditions. An additional or final seal in the form of a cover, such as a cover plate, is provided for the opening and finally seals the area of the opening. The additional or final seal is formed in a final vacuum welding stage which welds the cover to the container. Before vacuum welding of the cover to the container, the cover can be applied to the container by attaching or fixing it to the container as by resistance heating dot welding. As a result of the use of two vacuum welding stages in accordance with the present invention, all weld seams which face the outside are produced according to the same welding process.

The present invention is based on the realization that the weld seam to be produced under vacuum for the final seal of the container in the area of the preliminary seal or first sealing means which is to prevent escape of gas under vacuum conditions from the opening, must have a distance from this preliminary seal large enough that the preliminary seal will not be adversely influenced by the vacuum welding process. This distance depends, of course, on the type of material employed for the preliminary seal, on the wall thicknesses involved, on the shape of the housing portions involved, and the like. The precise value of the distance likewise can be determined empirically for the particular structure at hand, the maintenance of the required sealing effect by the preliminary seal being a criterion which can be monitored easily.

If the distance between the preliminary seal and the weld seam which finally seals the area of the opening were selected too small, there would exist the danger that the material of the preliminary seal would melt and, as a result of the excess pressure existing in the interior of the housing, with respect to an external vacuum such as formed during the final vacuum welding stage, the preliminary seal would be pressed out so that an undesirable pressure compensation could occur. Deformation of the preliminary seal under thermal influence, however, may be quite desirable during the work preparatory to final sealing. At a time when the housing is not as yet subjected to the vacuum for the final welding process, i.e. the pressure conditions are still equalized, a deformation of the means forming the preliminary seal has the result that its sealing effect is even improved by having the deformation cause the sealing means to adapt themselves particularly well to the shape of the opening. However, the heat intake in this case must be controlled so that the deformation of the sealing means does not go so far that parts of the opening will be exposed again. The basic idea is thus that the forces and thermal influences to be exerted during manufacture of the preliminary seal, and perhaps during the application and/or fixation of the cover which seals the area of the preliminary seal and is later welded to the remaining housing under vacuum, should be forces and influences which improve the sealing effect of the preliminary seal, while during final sealing under vacuum the preliminary seal must be influenced as little as possible.

In the various embodiments of the method according to the present invention, there principally exist three different ways of producing a preliminary seal by means of sealing means. These ways may also be combined, if required, in which case the respectively realized sealing effects are then superposed. These three different techniques are as follows:

1. Before application of the cover, a sealing means is used as a preliminary seal which is applied completely separately from the cover and which adequately performs its sealing action without the presence of the cover. For example, the opening can be preliminarily sealed by soldering, by casting shut with plastic or metal, or by means of resistance welding.

2. The sealing means are produced during application of the cover plate or they develop their full effect only when the cover plate is applied. In this embodiment, the sealing means can take the form of separate sealing elements which can be inserted into the opening, or the housing can be provided with sealing faces against which the cover plate is pressed, or special sealing elements can be provided which are connected with the cover plate.

3. The sealing means forming the preliminary seal is produced by a weld in the cover plate in a region surrounding the opening by direct passage of current by means of resistance welding.

In all cases, the final welding of the housing is effected, in coincidence with the welding process used otherwise, so that during this final welding process, the effect of the sealing means which produces the preliminary seal is not adversely influenced.

The cover may be applied to the container either from the outside of the container or it may seal the opening from the inside of the container, in which case a protrusion must extend to the outside through the opening of the container to hold the cover during welding. Depending on the circumstances, the weld seam which forms the final seal toward the outside may be disposed, with respect to the surface of the container, to correspond with the spatial configuration either outside or inside the region of the sealing means forming the preliminary seal.

In all embodiments of the method according to the present invention, the container components are welded together under vacuum in the first welding stage to such an extent that generally only one opening remains, and through this remaining opening the interior of the container can be filled with a medium under the desired pressure. In the embodiment which relates to the sealing of cardiac pacemaker housings made of a cobalt alloy, two housing half cups are connected together under vacuum by means of a weld seam produced by electron beam welding. The electronic circuitry and the batteries and further components required for the operation of the pacemaker are inserted into the housing before this initial welding stage. Only one opening remains which has a circular cross section with a diameter at about 0.8 mm. Through this opening, the interior of the cardiac pacemaker is filled with helium at atmospheric pressure, which helium may also serve later to test the sealed housing for tightness.

The final sealing of the housing of the cardiac pacemaker may be accomplished in various ways, which will be explained in various embodiments of the method according to the present invention, as illustrated in FIGS. 1 through 7 where reference numeral 1 indicates the housing. The primed reference numerals in the figures correspond to similar parts for the different embodiments of the invention. In the figures, the housing interior is always disposed toward the bottom. The medium under atmospheric pressure is marked M.

In FIG. 1, housing 1 is a housing which has been formed during an initial vacuum welding stage which has closed all outside openings except for one remaining opening 2. The vacuum of the initial welding stage is then removed, and the interior of housing 1 is filled with a gaseous medium under atmospheric pressure. In FIG. 1, after the interior is filled with a gaseous medium, opening 2 is sealed with a sealing means 3 which may be done by soldering with solder, by welding with a drop of the material used for welding, or by casting with metal or plastic. The material for sealing means 3 must be selected so that it is resistant to the internal pressure of the medium introduced into the housing when the housing is placed under an external vacuum such as occurs during the final vacuum welding stage. After forming sealing means 3, the area of the opening 2 is covered by means of a cover plate 4 which is fixed along its edge, in the area of a later weld seam 5, by means of weld dots applied by resistance welding. Heating produced during this resistance welding must not adversely affect the sealing effect of sealing means 3. The size of cover plate 4 must therefore be selected so that heating or mechanical stresses during positioning and fixing of the cover plate 4 are transmitted only within limits to sealing means 3. It must be considered that pressing of cover plate 4 or slight heating in its central region may have the result of an improved sealing effect of sealing means 3 due to improved form fit. This process can be enhanced, for example, by having sealing means 3 slightly protrude over the surface of housing 1 in the area of opening 2, so that the pressing effect of cover plate 4 on the surface of sealing means 3 produces an additional tendency to press sealing means 3 into opening 2. After cover plate 4 is fixed to housing 1 by weld dots, the cover plate 4 is sealed along its edge to housing 1 by welding under vacuum which produces weld seam 5.

Figure 2:
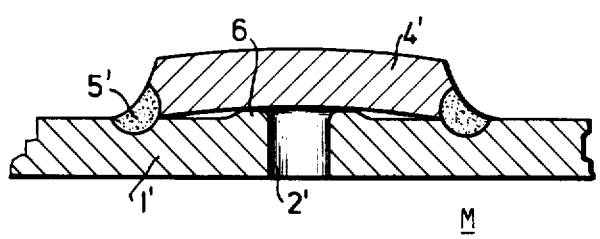
FIG. 2 is a corresponding view for a second embodiment of the method according to the present invention.

In the housing 1' shown in FIG. 2, which has been sealed according to another embodiment of the method according to the present invention, an opening 2' is provided with a circumferential bead 6 which may be produced, for example, by punching or stamping of a bore. When cover plate 4' is applied, the peak region of circumferential bead 6 encircles opening 2', contacts the underside of cover plate 4', and forms the preliminary seal for opening 2' of housing 1'. As in the other embodiments of the method, the cover plate 4' is brought into position once the internal and external pressures have become equalized, i.e. the housing to be filled with a medium, for example a gas, has been immersed into this medium. If during fastening of the cover plate 4' before the final vacuum welding, a pressure is exerted in the direction toward circumferential bead 6, the peak region of bead 6 is flattened due to the high areal compression and thus produces improved sealing capability. This effect can be increased by fastening cover plate 4' to housing 1' by a heating process, such as by dot welding along its edges, in the area of a later weld seam 5', and supplying enough heat during this heating process to the extent that the circumferential bead 6 becomes slightly plastically deformable. Care must then be taken, however, that the deformability due to thermal influence does not again produce a decrease in the sealing effect of the preliminary seal. Further, in the area of bead 6, housing 1' may be connected with cover plate 4' by electric resistance welding.

Once a preliminary seal of housing 1' has thus been obtained in the appropriate manner, the final welding of cover plate 4' can be effected under vacuum by means of electron beam welding and, due to the sufficient distance between the weld seam 5' produced by the final welding and the locus of the preliminary seal it is assured, by the method according to the present invention, that the sealing effect of the preliminary seal remains intact during the welding process.

Figure 3:
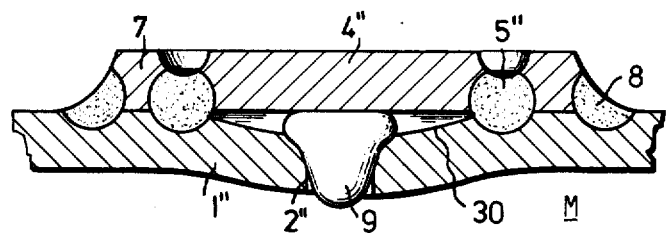
FIG. 3 is a corresponding view for a third embodiment of the method of the present invention.

FIG. 3 shows a corresponding portion of a housing 1" sealed according to a further embodiment of the method according to the invention.

In this embodiment, the region of the container surrounding the opening forms a groove which is designed so that the first sealing means is flush with the region of the container which encircles the groove. Thus, as shown in FIG. 3, housing 1" is provided with a groove 30 in the region of an opening 2", which groove equalizes the amount by which the sealing means used for sealing opening 2" would protrude beyond the outer contour of housing 1". In this way, it is possible to use a planar cover plate 4". A difference in height produced by the sealing means can also be compensated for in a corresponding manner by an outer curvature of the cover plate 4".

The housing of the container may be formed or machined with a recess so that a flat cover plate, when in place, is flush with the housing outside. This improves the weld joint by allowing greater weld penetration in the area of the edge of the cover plate.

In order to facilitate fixing and later welding of cover plate 4", housing 1" is provided with a ring 7 adapted to cover plate 4" in the area of opening 2", the ring enclosing cover plate 4". This ring 7 is fastened to housing 1" by a weld seam 8 formed during the first or initial welding stage of the housing under vacuum. The further operation of ring 7 will be explained in detail below.

In the embodiment of the method illustrated in FIG. 3, a metal member 9 which is tapered in the direction toward the interior of the housing (toward the bottom in the drawing) serves as the sealing means which is pressed by the cover plate 4" against the facing edge of opening 2". FIG. 3, as well as FIGS. 1, 2, 6 and 7, show the final state of the welded container. The metal member 9 then has its deformed state.

Figure 4:
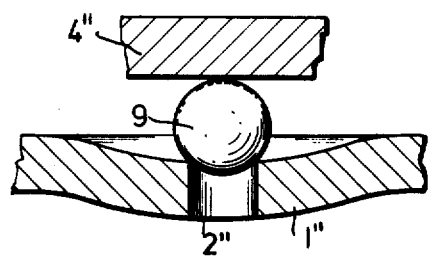
FIG. 4 is a sectional view of the illustration of FIG. 3 for an earlier process step.

In the illustrated embodiment of FIG. 3, member 9 originally has the shape of a sphere, as can be seen in FIG. 4. FIG. 4 shows a section of the housing area shown in FIG. 3 in which, however, cover plate 4" has not as yet been fixed in its position by resistance welding. Member 9, which in FIG. 4 still has its spherical shape, is placed into opening 2" and cover plate 4" is positioned on top of it. Instead of the spherical shape, member 9 may also have any other shape which tapers in the direction toward opening 2", such as, for example, a conical shape. The shape of member 9 must be adapted to the shape of the cross section of opening 2" in such a manner that the preliminary seal forms a closed curve. Member 9 may also be permanently connected with cover plate 4" or manufactured together with it.

The use of a spherical shape for member 9 has the advantage of particularly easy manufacture and can be obtained in conventional types of materials for various diameters of opening 2". The diameter of the sphere will advisably be selected to be about 20% larger than the diameter of opening 2", which in order to fit the spherical shape must have a circular cross section. In the present embodiment illustrated in FIG. 4, the sphere has a diameter of 1 mm and opening 2" has a diameter of 0.8 mm. There again results a high areal pressure at the edge of opening 2" which comes in contact with the sphere, and during pressing down of cover plate 4", this results in a high specific deformation of the material and in the formation of suitably expanded sealing surfaces. In a preferred embodiment of the invention, sealing means, housing and cover plate are made of the same material, which results, on the one hand, in long life of the housing, even in aqueous solution, since no galvanic elements can form. On the other hand, the properties with respect to deformation, current and heat conduction can also be optimally adapted in such a case.

After spherical member 9 has initially been put in place loosely, cover plate 4" is inserted into the space bordered by ring 7, as shown in FIG. 3, and is there fixed in place. The pressure exerted by cover plate 4" holds member 9 in position and presses it against the edge of opening 2" so that the desired sealing effect can be attained once the cover plate 4" is fixed in position. Fixing of cover plate 4" along its edges by means of a few dot welds made by way of resistance welding in the area of a later weld seam 5" produces a thermal effect with which the resulting sealing effect can be improved further. Heating of member 9 during resistance welding is effected on the one hand by the flow of current through the member itself, and on the other hand by heat conduction from the regions of greatest heating in the area of weld seam 5". The simultaneous effect of pressure and heat finally changes the spherical shape to the mushroom shape shown in FIG. 3 which assures a particularly good preliminary seal. The degree of deformation of member 9 may be determined over a wide range by selection of external parameters and depends on the respective case of use and on the quality of the preliminary seal required for it. As shown in FIG. 3, the sphere in its final position is supported between the opening and the cover plate.

Weld seam 5" is produced during a welding under vacuum in which the final outer seal is established. This weld seam is also present in the region of the bottom of the V-shaped cross section formed by the outer edge of cover plate 4" and the inner edge of ring 7. Due to the fact that during the final vacuum welding process, the material of ring 7 is also available for the bond, the danger of melting through the housing during vacuum welding to produce weld seam 5" is avoided even with relatively thin pieces of housing material, especially as compared to the danger of melting through that occurs with weld seams 5 and 5' shown in FIGS. 1 and 2, so that ring 7, together with facilitating fixation of cover plate 4", performs a dual function. In FIG. 3, the dimensions are also selected according to the invention so that during final welding of cover plate 4", member 9 will not be heated to such an extent that the sealing effect of member 9 would be impaired and the medium contained in the interior of the housing could escape.

Figure 5:
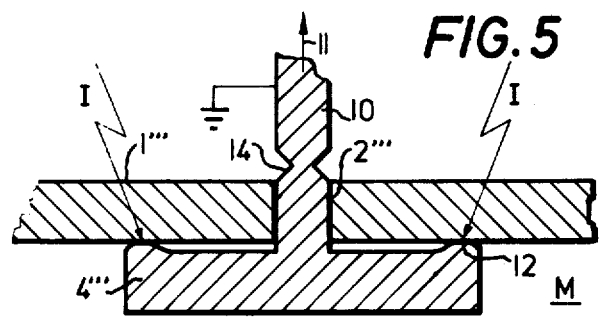
FIG. 5 is a sectional view for a fourth embodiment of the method according to the present invention, and illustrates a step of the process before final welding.
Figure 6:
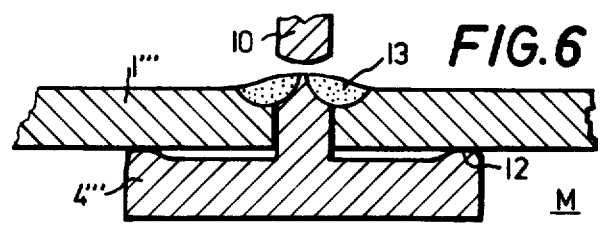
FIG. 6 is a view of the illustration of FIG. 5, but afteer final welding under vacuum.

Turning now to FIGS. 5 and 6, the portion of a container shown in these Figures is produced according to a further embodiment of the method according to the invention. In FIGS. 5 and 6, there is shown a housing 1''' and a cover plate 4''', which when finally sealed, is substantially in the interior of the container. Cover plate 4''' has a protrusion 10 thereon which extends through an opening 2''' to the outside of housing 1'''. Cover plate 4''' further contains a circumferential bead 12. Cover plate 4''' is inserted into the interior of housing 1''' before the latter has been sealed by welding under vacuum during the first vacuum welding stage which maintains opening 2'''. Cover plate 4''' can then be held in position by means of protrusion 10. The preliminary seal is produced by the exertion of a pulling force in the direction of arrow 11 so that cover plate 4''' is pressed from the inside against housing 1''' in the region of circumferential bead 12. Cover plate 4''' has a circular cross section so that bead 12 forms a circular ring which encircles opening 2'''.

The gas inside the housing 1''' is removed by vacuum pumping in a chamber. The filling is accomplished by backfilling the chamber with a gaseous medium filling the housing through a space located between protrusion 10 and housing 1'''. This space is large enought to provide electrical insulation from housing 1''' during the subsequent resistance welding that takes place.

In the region of this circular ring, once the interior of housing 1''' has been filled with a gaseous medium substantially under atmospheric pressure, a circumferential weld which forms the preliminary seal is formed by resistance welding, using a current I so that during the subsequent final sealing of housing 1''' by means of welding under vacuum, the medium can no longer escape. Protrusion 10 of cover plate 4''' has a cross section in the region of opening 2''' which is adapted to that opening so that the final seal of housing 1''' from the outside can be produced by a weld seam 13 around this protrusion 10, which weld seam is produced under vacuum by electron beam welding. The resulting weld seam 13 is shown in section in FIG. 6. A circumferential groove 14, shown in FIG. 5, in protrusion 10, makes it possible for the portion of protrusion 10 which protrudes beyond the surface of housing 1''' to be removed with particular ease after the vacuum welding process or it melts away already during the vacuum welding process, respectively. Due to the fact that cover plate 4''' is disposed in the interior of housing 1''', this embodiment of the method according to the invention is particularly advantageous for producing a particularly planar outer surface of the container which has no protruding parts. The means required for two-stage vacuum weld sealing are then hardly discernable from the outside.

Commercially available welding machines, such as, for example, the Electron Beam Welding Machine made by Wentgate Engineers Ltd., St. Ives, Huntingdonshire, Great Britain, can be used for the electron beam welding under vacuum. The required settings to take care of the materials to be welded and their dimensions are listed in the service manual for this machine supplied by its manufacturer.

Figure 7:
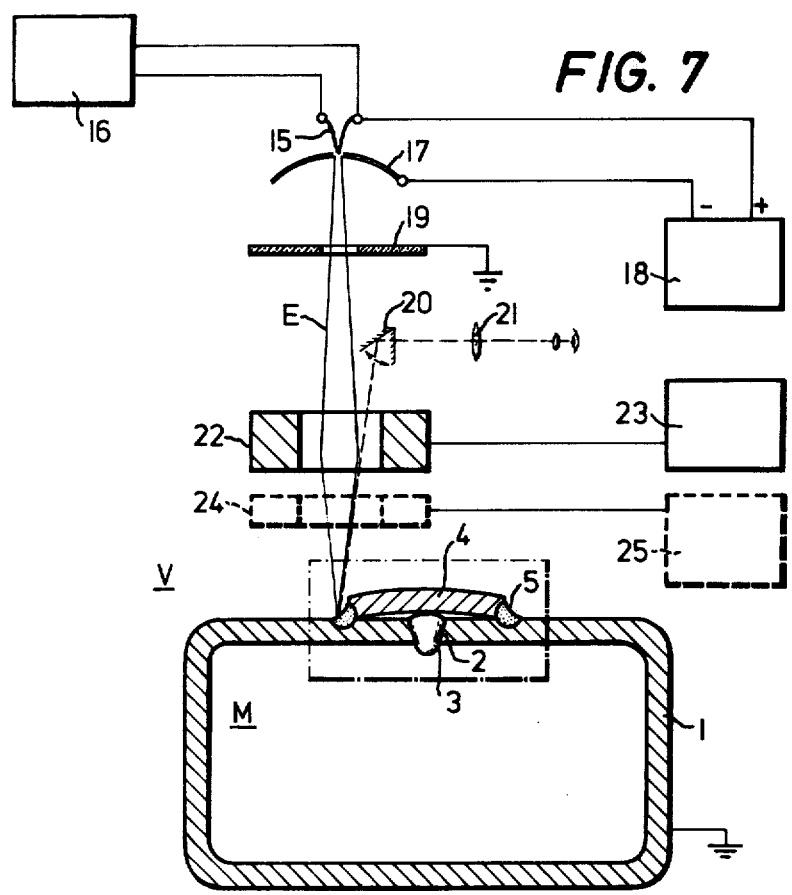
FIG. 7 is a schematic view of an electron beam welding process under vacuum according to the present invention.

FIG. 7 shows such an electron beam welding device during production of weld seam 5 of FIG. 1 which finally seals housing 1 from the outside, the device operating under a vacuum V. The section of housing 1 shown in FIGS. 1 through 6 is outlined in FIG. 7 by a dot-dash line. An electron beam E emanates from a heating filament 15 whose heating current and high voltage are supplied by a source 16. A grid 17 which has a negative potential with respect to the heating filament 15 forms a cathode, is connected to a voltage source 18, and sets the operating point of the electron beam. An anode 19 is at ground potential. The welding process can be observed by means of a mirror 20 and an ocular 21. A magnetic lens 22 which is connected to a constant current source 23 effects focusing of the electron beam. If necessary, magnetic deflection means 24 may be provided which make it possible to deflect the electron beam in the working plane in the x and y directions in dependence on a deflection control device 25 so as to vary the locus of the weld with a fixed workpiece. In the schematic illustration of FIG. 7, housing 1 is shown greatly enlarged with respect to the welding device.

The illustrated embodiments of the method according to the invention are intended to demonstrate that the principle on which the invention is based covers a large number of embodiments in which the selection of the appropriate dimensions and the setting of welding parameters is of significance but lies, according to the above explanations, within the range of the skill of the average artisan.

It will be understood that the above description of the present invention is susceptible to various modifications, changes and adaptations, and the same are intended to be comprehended within the meaning and range of equivalents of the appended claims.

What is claimed is:

1. Method for producing a container whose interior is substantially under atmospheric pressure by means of a vacuum welding process, comprising:
   (a) assembling the container by welding under vacuum a plurality of wall components while maintaining an opening in the container;
   (b) filling the interior of the container through the opening with a medium which is substantially under atmospheric pressure;
   (c) sealing the opening of the filled container to be vacuum-tight by means of a first sealing means; and
   (d) sealing the container interior from the outside by an additional seal in the form of a cover for the opening by vacuum welding the cover to the container, with the cover bordering the outer surface of the container in such a manner that the cover is welded under vacuum to the container along a line which extends at such a distance from the first sealing means that the sealing effect of the first sealing means is not adversely influenced during the vacuum welding of the cover.

2. Method as defined in claim 1 wherein the welding under vacuum is effected by an electron beam welding process.

3. Method as defined in claim 1 wherein the opening is preliminarily sealed by soldering, resistance welding or casting.

4. Method as defined in claim 1 wherein the cover is applied to the container before said cover is vacuum welded to the container, and wherein pressure and/or temperature influences are transmitted to said first sealing means during the application of said cover to produce an at least improved sealing effect by adapting the shape of said first sealing means to the opening.

5. Method as defined in claim 1 wherein the cover is fixed to the container by resistance welding before the cover is vacuum welded to the container.

6. Method as defined in claim 5 wherein the heating during resistance welding is selected so that an at least improved sealing effect is realized by adaptation of the shape of said first sealing means to the opening.

7. Method as defined in claim 5 wherein the cover is connected with the container by means of resistance welding along a line enclosing the opening, the resistance welding producing a weld seam which forms said first sealing means.

8. Method as defined in claim 7 wherein the cover is inserted into the interior of the container before the container is welded shut during step a), the cover is placed in a final position against the inside of the container, and the cover has a protrusion which, once the cover has taken up its final position, protrudes toward the outside through the opening in the container.

9. Method as defined in claim 8 wherein the protrusion is provided with a groove which, when the protrusion is in its final position, is disposed in the vicinity of the outer surface of said container.

10. Method as defined in claim 1 wherein the opening is sealed by contacting surfaces which form said first sealing means.

11. Method as defined in claim 10 wherein the housing has a circumferential bead which encircles the opening and which rests against the cover.

12. Method as defined in claim 11 wherein the circumferential bead is produced by stamping.

13. Method as defined in claim 10 wherein the cover has a circumferential bead which encircles the opening and which rests against the interior of the container.

14. Method as defined in claim 1 wherein a member which tapers in the direction toward the opening and constitutes said first sealing means is inserted into the opening.

15. Method as defined in claim 14 wherein the member which tapers in the direction toward the opening is connected with the cover or forms a part thereof.

16. Method as defined in claim 14 wherein the tapered member is a sphere, the opening has a circular cross section, and the sphere in its final position is supported between the opening and the cover.

17. Method as defined in claim 1 wherein the region of the container surrounding the opening forms a groove which is designed so that said first sealing means is flush with the region of the container which encircles the groove.

18. Method as defined in claim 1 wherein the container is provided with a ring which surrounds the cover.

19. Method as defined in claim 18 wherein the cover is welded under vacuum in the area of adjacent edges of the cover and the surrounding ring.

20. Method as defined in claim 1 wherein the sealing during step (a) leaves the container with only one opening for filling the container with the medium.

* * * * *